United States Patent [19]

Miller

[11] Patent Number: 5,014,724
[45] Date of Patent: May 14, 1991

[54] PEDIATRIC IMMOBILIZATION DEVICE

[76] Inventor: Larry C. Miller, P. O. Box 784, La Canada, Calif. 91011

[21] Appl. No.: 529,556

[22] Filed: May 29, 1990

Related U.S. Application Data

[63] Continuation of Ser. No. 345,765, May 1, 1989.

[51] Int. Cl.$^5$ ............................ A61F 5/37; A61G 1/00
[52] U.S. Cl. ...................................... 128/870; 5/82 B; 5/82 R
[58] Field of Search ............... 128/846, 869, 870, 876; 5/81 R, 81 B, 82 R

[56] References Cited

U.S. PATENT DOCUMENTS

| | | | |
|---|---|---|---|
| 2,410,181 | 10/1946 | Peters | 5/82 |
| 2,788,530 | 4/1957 | Ferguson | 5/82 R |
| 3,889,668 | 6/1975 | Ochs | 128/870 |
| 4,151,842 | 5/1979 | Miller | 5/82 B |
| 4,211,218 | 7/1980 | Kendrick | 128/870 |
| 4,299,211 | 11/1981 | Doynow | 128/870 |
| 4,566,445 | 1/1986 | Jelsma | 5/82 R |
| 4,601,075 | 7/1986 | Smith | 128/870 |
| 4,665,908 | 5/1987 | Calkin | 5/82 R |
| 4,736,474 | 4/1988 | Moran | 5/82 R |
| 4,895,173 | 1/1990 | Brault | 128/870 |

Primary Examiner—Robert A. Hafer
Assistant Examiner—Michael Brown
Attorney, Agent, or Firm—James E. Brunton

[57] ABSTRACT

A pediatric immobilization apparatus for use in emergency treatment of pediatric accident victims prior to, and while being transported to an appropriate medical facility. The apparatus includes a rigid support panel covered by a washable fabric covering to which strategically located restraining straps, and shoulder harnesses are interconnected. The device can be used alone or in conjunction with a widely used prior art adult splint and litter device of special configuration.

7 Claims, 2 Drawing Sheets

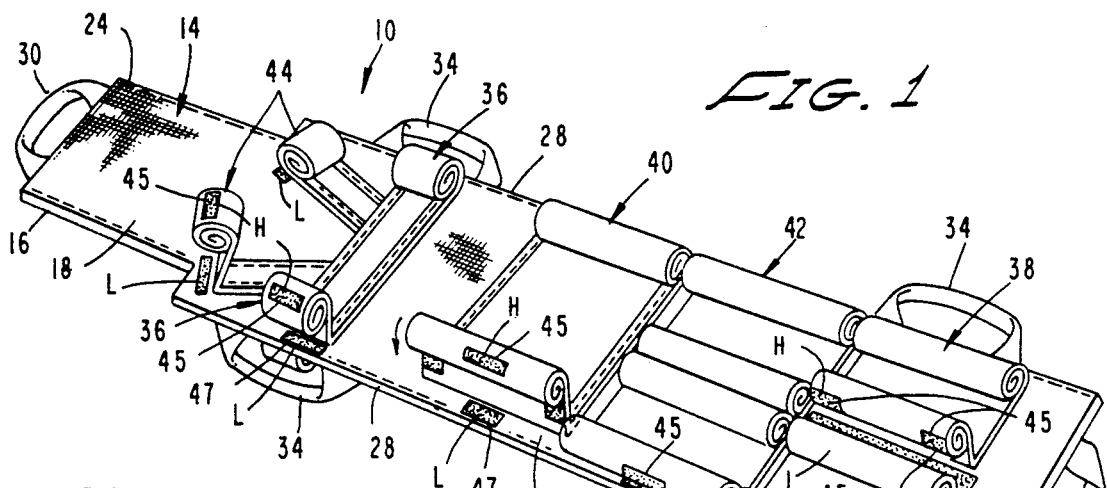
FIG. 1
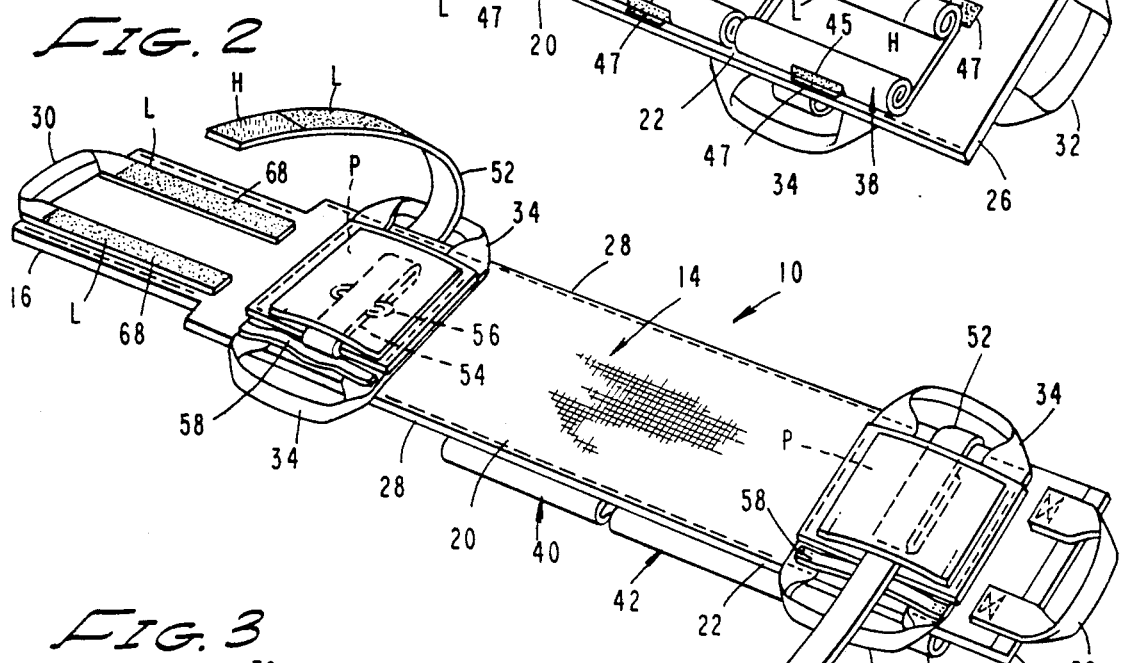
FIG. 2
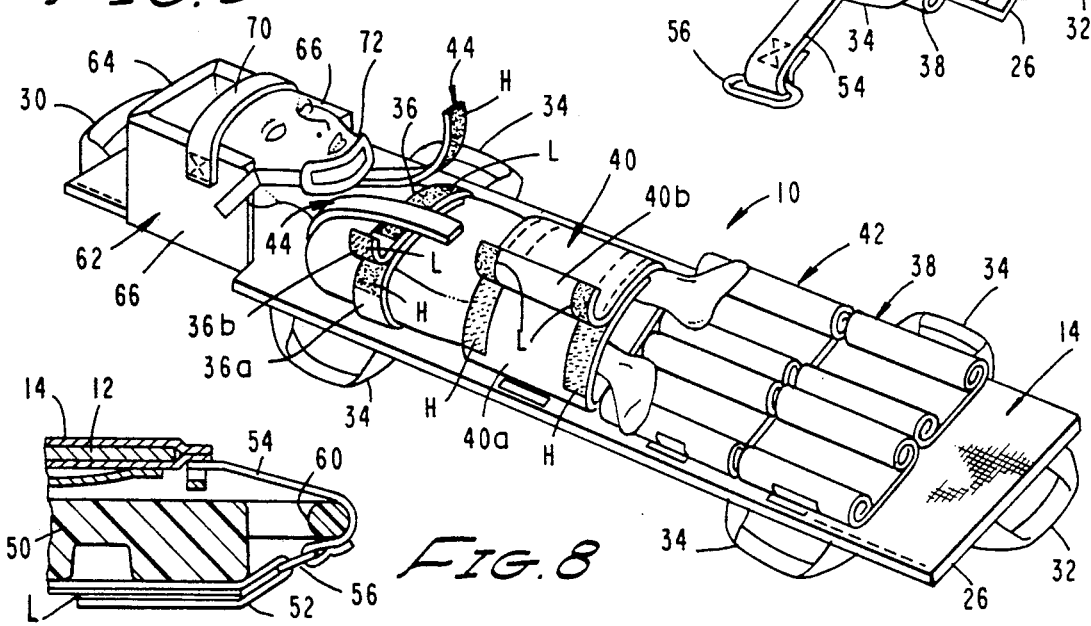
FIG. 3
FIG. 8

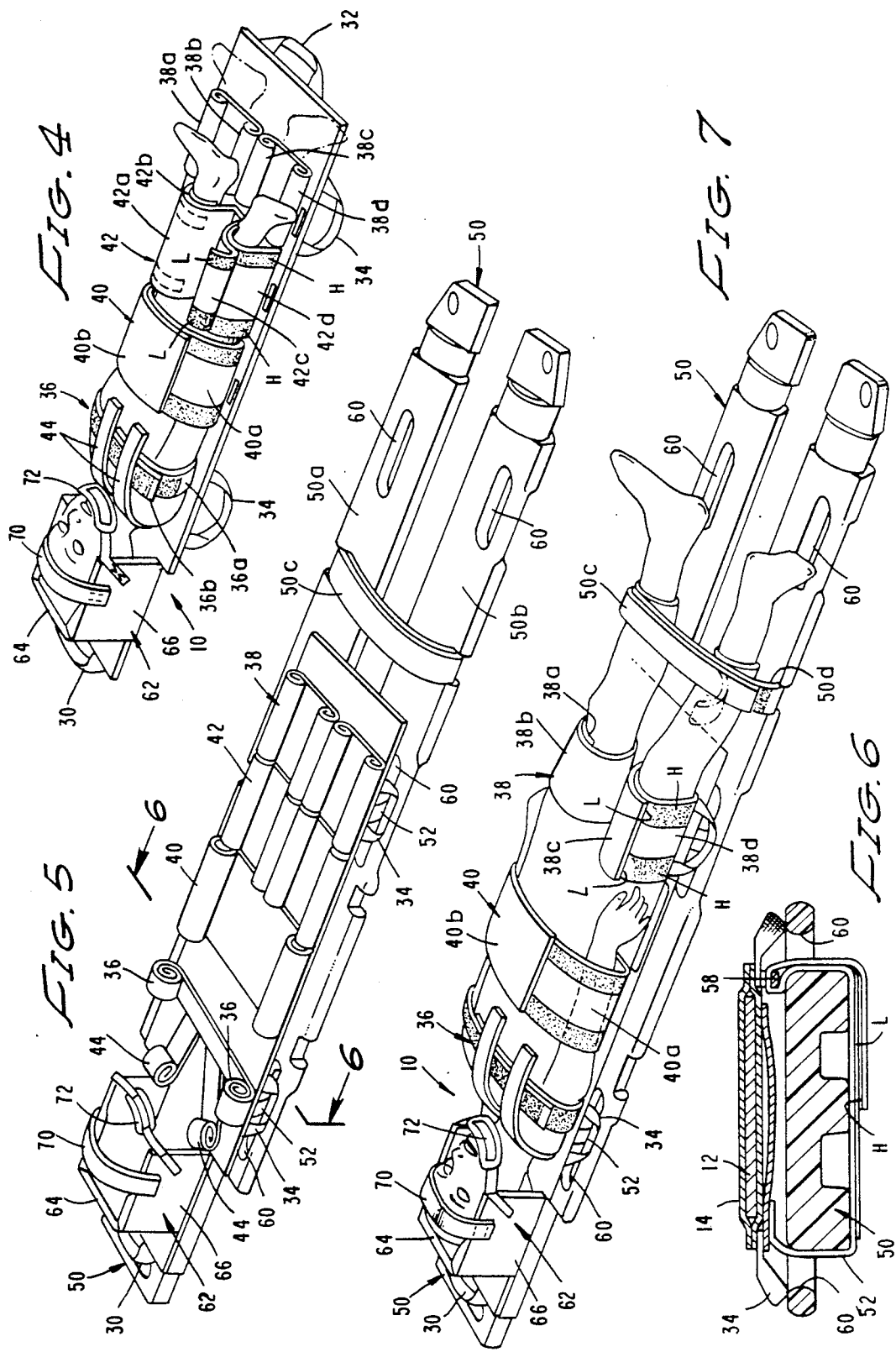

PEDIATRIC IMMOBILIZATION DEVICE

This application is a continuation of application Ser. No. 345,765, filed May 1, 1989.

BACKGROUND OF THE INVENTION

1. Field of The Invention

The present invention relates generally to an apparatus for immobilization of pediatric accident victims prior to, and while being transported to an appropriate medical facility. More particularly, the invention relates to a body splint and litter apparatus usable both in the field and within a medical facility having a rigid support panel covered by a washable fabric covering to which strategically located restraining straps and shoulder harnesses are interconnected. The device can be used alone or in conjunction with a widely used adult splint and litter device of special configuration.

2. Description of the Prior Art

Many forms of emergency body splint or litter types of apparatus have been used by medical and rescue personnel over the years. For years these devices were extremely crude and comprised little more than a stretcher. In relatively recent times, it was realized that extreme caution was necessary in any attempted movement of an injure victim. Improper movement often resulted in further injury to the victim, the effects of which ranged from contributing to a prolonged recuperation period, to causing irreparable damage to the injured party.

One of the most successful body splint and litter devices to be developed in recent years is described in U.S. Pat. No. 4,151,842, issued to the present inventor. This device has been widely used and has enjoyed great commercial success.

Since the development of the aforementioned device, it has been recognized that a vital need exists for a body splint and litter device which is specifically designed for use in the emergency handling and transport of infants and small children. It is this need to which the present invention is directed.

Although the device of Pat. No. 4,151,842 is ideally suited for use with adult patients, it is not particularly well suited for use with infants and small children. For example, the proportions of the rigid support panel of the adult device and the location of the restraining straps are specifically designed to positively support, and suitably restrain, the larger body of an adult. Accordingly, the device does not properly accommodate infants and children having much smaller body sizes.

In designing the device of the present invention, it became immediately apparent that much more was required than merely down sizing the adult apparatus to fit a child. For example, one problem faced by the inventor was attempting to design an apparatus which would accommodate children varying in size from a small baby to a child considerably larger than a baby, but still too small to be accommodated by the adult size apparatus. More particularly, the size, number and location of the restraining straps of the pediatric device had to be carefully considered so as to provide safe restraint to the head, neck, shoulders, and upper and lower torso of patients of widely varying body sizes.

In the design of the pediatric unit, it was realized that to properly provide for all children too small for accommodation by the adult apparatus, the ideally sized pediatric device should be specially adapted for use in conjunction with the device of Pat. No. 4,151,842. This feature comprises an important aspect of the apparatus of the present invention. As will be better understood from the description which follows, the device of the present invention is specifically configured and designed to enable it to be expeditiously used with the apparatus of Pat. No. 4,151,842 in a manner to accommodate children of relatively large stature.

When only the pediatric apparatus of the invention is used, the restraining straps are uniquely sized and arranged so that they can be selectively used to safely restrict the movement of children ranging in age from a few months to several years. When the pediatric device is used in conjunction with the adult sized apparatus, the device is strategically configured to fit between the head portion and the leg extensions of the apparatus in a manner so as not to interfere with the handling of the apparatus and its emplacement within standard basket type litters having leg dividing partitions. Further, the width of the pediatric device is such that it will fit between the hand receiving, lifting apertures of the adult apparatus in a manner not to interfere with the lifting and transport of the combined units. Additionally, the length of the pediatric device is such that it will not interfere with the use of the lower restraining straps on the adult apparatus to immobilize the legs of larger children.

SUMMARY OF THE INVENTION

It is an object of the present invention to provide a pediatric immobilization board for use with infants and small children that will support the head, neck, shoulders, upper and lower torso, and legs in a manner so as to securely immobilize the child during treatment and transport to a medical facility. The device can also be used as a restraint board in the hospital to restrict the movement of an infant or small child during medical procedures.

Another object of the present invention is to provide a pediatric immobilization board of the aforementioned character which is suitable for use in combination with an adult body splint and litter board of the type commonly used in rescue operations for supporting the body while being transported.

It is another object of the invention to provide a pediatric immobilization board of the class described having strategically located, flexible straps for supporting the full body of the infant, including a harness for restricting motion of the head of the infant during transport.

A further object of the invention is to provide a pediatric device as described in the preceding paragraphs which can accommodate children ranging in age from a few months to several years and ranging in weight from a few pounds to about sixty-five pounds.

Another object of the invention is to provide a pediatric splint and litter in which the restraining straps are specially configured and located so as to permit a small child to breathe, even if the strap over the infant's chest is inadvertently drawn too tight. Similarly, a pair of leg restraining straps are provided and strategically located so that on a very small child the upper leg straps can be used to secure the legs without the lower straps being used.

Yet another object of the invention is to provide a pediatric device of the class described which is radio-transparent and includes an easily removable washable fabric covering, to which lifting handles are connected at the sides and at each end to permit lifting in both a horizontal and vertical direction.

Another object of the invention is to provide a pediatric device having a unique harness system that will completely immobilize the spine and allow the manipulation of the child in any position to maintain an air way for radiological and other medical procedures.

Another important object of the invention is to provide a pediatric device which can be quickly secured to the device described in U.S. Pat. No. 4,151,842 in a manner such that the combination thus formed can be used with stretchers and basket type litters, including the standard Navy litter with leg partitions, can safely be used in helicopter transport, and can also be used as a flotation rescue device.

It is still a further object to provide an infant body splint and litter device that is economical to manufacture and use, as well as being safe, rugged, reliable and easy to operate and adjust without specialized training.

BRIEF DESCRIPTION OF THE DRAWINGS

FIG. 1 is a generally perspective top view of the pediatric immobilization device of the present invention.

FIG. 2 is a perspective bottom view of the immobilization device.

FIG. 3 is a perspective view, similar to FIG. 1, but showing a small child immobilized within the immobilization device of the present invention.

FIG. 4 is a generally perspective view, similar to FIG. 3, but showing a slightly larger child immobilized on the device of the invention.

FIG. 5 is a generally perspective view illustrating a pediatric immobilization device of the present invention interconnected with an adult splint or litter device of the general character described in U.S. Pat. No. 4,151,842.

FIG. 6 is a cross sectional view taken along lines 6—6 of FIG. 5 showing the method of interconnection of the pediatric device of the present invention with the adult splint or litter device.

FIG. 7 is a generally perspective view, similar to FIG. 5, but showing still a larger child immobilized on the combined pediatric immobilization device and the adult splint or litter type device.

FIG. 8 is a fragmentary cross sectional view similar to FIG. 6 illustrating the manner in which the pediatric device is interconnected with a wide adult size litter device.

DESCRIPTION OF THE INVENTION

Referring to the drawings, and particularly to FIGS. 1 and 6, the pediatric immobilization device of the present form of the invention 10 comprises a rigid panel 12 (FIG. 6) encapsulated within a cover means, shown here as a fabric cover 14, which substantially conforms the shape of the rigid panel 12. The covered, rigid panel forms a body support having a head, neck, body, and leg portion 16, 18, 20 and 22, respectively. As best seen in FIG. 1, the body portion of the device is greater in width than the head and neck portion and is of an overall length sufficient to support the body of a small child. Typically, the overall length of the pediatric immobilization device of the invention is on the order of three to four (3 to 4) feet. The cover 14, which encapsulates the rigid panel 12, is preferably constructed of a durable, washable material such as nylon, rayon or canvas. The selected cover material should be easy to clean and disinfect, and yet durable enough to withstand harsh treatment, either n the field or in the hospital. The rigid panel is preferably made of marine finished plywood so as to be easy to clean and maintain when removed from cover 14.

The cover 14 includes top, bottom and sides 24, 26 and 28, respectively. Connected proximate the top and bottom of the cover are carrying straps 30 and 32 for lifting the device in a vertical direction. For example, if the injured child needs to be lifted up a steep incline or from a well or other enclosure, the entire device, with the child immobilized thereon, can be conveniently lifted upwardly by grasping the flexible carrying strap 30. Similarly, if more convenient, the device can be lifted vertically, or at a steep incline, by grasping the bottom strap 32. Longitudinally spaced apart side straps 34 are used for carrying the immobilization device in a generally horizontal position. The carrying straps 34 are connected to cover 14 and are strategically positioned so that two men, one on each side of the device, can grasp the carrying straps 34 and conveniently transport the device with the patient being maintained in a substantially horizontal orientation.

An important aspect of the device of the present invention is the patient restraining means which comprises a plurality of strategically located restraining straps which function to safely restrain the child in an immobilized condition upon the device. More particularly, a first set 36 of flexible restraining straps are connected to cover 14 proximate the upper portion thereof and a second set 38 of straps are connected to cover 14 proximate the bottom portion thereof. It should be noted that the second set 38 comprise straps that are substantially wider than the straps of strap set 36. A third set 40 of flexible restraining straps are disposed intermediate first and second sets of straps 36 and 38. The straps which comprise strap set 40 are also of a width substantially greater than the width of the straps of set 36.

A fourth set 42 of flexible restraining straps are disposed intermediate second and third sets of straps 38 and 40. Finally, a set 44 of angularly extending flexible shoulder straps are connected to the cover and are disposed proximate the first set of straps 34. The shoulder straps function to restrain the shoulders of the infant or child in the manner shown in FIGS. 3, 4 and 7.

Referring particularly to FIG. 3, each of the straps of sets 36 and 40 comprise a first strap designated in FIG. 3 by the numerals 36a and 40a. Each strap 36a and 40a is provided with connector means shown here as a fabric having multiplicity of hooks H disposed on ne side of the strap. Similarly, each set of straps 36 and 40 has a second strap designated in FIG. 3 by the numerals 36b and 40b. These straps are also provided with interconnection means for interconnecting the straps with straps 36a and 40a, respectively. The interconnection means are here provided as a fabric having multiplicity of loops L which can be releasably interconnected with hooks H. While various types of interconnection means can be used without departing from the scope of the present invention, a material manufactured and sold under the name and style VELCRO has proven to be satisfactory. Turning to FIG. 4, it can be seen that strap sets 38 and 42 each comprise 2 straps which cooperate to encapsulate the legs of the patient. In FIG. 4, the straps are designated by the numerals 42a, 42b, 42c, and 42d, and 38a, 38b, 38c, and 38d, respectively. Each pair of straps of each set of straps is provided with interconnection means shown here as hook and loop connectors H and L, respectively of the character previously described herein (See also FIG. 7).

Referring, again, to FIGS. 1 and 3, each of the shoulder straps 44 is provided with interconnection means on the under surface thereof shown in FIG. 3 as a multiplicity of hooks H. Hooks H are adapted to releasably interengage a multiplicity of loops L provided on the upper surface of strap 36b of strap set 36. With this arrangement, after straps 36a and 36b have been passed over the infant's chest, the shoulder straps can be snugly passed over the infant's shoulders in the manner shown in FIG. 3 and releasably interconnected with strap 36b.

As best seen in FIG. 1, each of the strap sets 36, 38, 40 and 42, as well as the shoulder straps 44, are provided with short sections 45 of connector means which are adapted to be releasably interconnected with short sections 47 of mating connector means carried on the upper surface of the cover 14. These connector means 35 and 47 are shown in the drawings as comprising short lengths of fabric having multiplicity of hooks H which releasably interconnect with a multiplicity of loops L. When the straps are not in use, these short sections of fabric function to hold the individual straps of the strap sets in a tightly rolled configuration as illustrated in FIGS. 1 and 5.

Referring now to FIG. 2, an important aspect of the present invention is the provision of connector means, shown here as longitudinally spaced pairs of elongated strap means which function to secure the pediatric immobilization device of the present invention to an adult body splint and litter device 50 of the character shown in FIG. 5. In the embodiment of the invention shown in the drawings, these elongated strap means comprise two longitudinally spaced flexible straps 52 which are interconnected to one side of cover 14 and two longitudinally spaced straps 54 connected to the opposite side of cover 14. Straps 54 include a strap receiving ring 56 provided at the outboard end of each strap. Also, forming a part of the connector means for interconnecting the pediatric immobilization device with the adult size device are a pair of longitudinally extending straps 58 which are affixed at either end to the underside of cover 14 and pass perpendicularly of straps 54.

Turning to FIG. 6, the use of straps 52 to interconnect the pediatric immobilization device with the adult device is there illustrated. When only straps 52 are used, as shown in FIG. 6, each strap is passed through a hand receiving aperture 60 formed in the sides of the adult size device 50 and extended underneath the device 50. The strap is then passed upwardly along the side of device 50 and then passed between strap 58 and the bottom of cover 14. Finally the strap is looped back upon itself, pulled tight and interconnected to itself in the manner shown in FIG. 6. As best seen in FIG. 2, the upper surface of each strap 52 is provided with a multiplicity of hooks H disposed proximate the outboard end of the strap and a multiplicity of loops L spaced inwardly from hooks H. With this arrangement, when strap 52 is looped back upon itself, in the manner shown in FIG. 6, hooks L can be releasably interconnected with loops L so as to securely interconnect the pediatric immobilization device with the adult device in the manner shown in FIGS. 5, 6, and 7.

When the adult splint and litter device has a width greater than that shown in the drawings, straps 52, may be too short to pass around the wider device. In such an instance, straps 52 are used in conjunction with straps 54 in the manner shown in FIG. 8 to removably interconnect the pediatric immobilization device with the adult size device. This method of interconnection is accomplished by passing strap 52 underneath the adult device, then through the strap receiving ring 56 and then back upon itself so that the multiplicity of hooks can be releasably interconnected with the multiplicity of loops L provided on strap 52. With this latter type of interconnection, adult size splint and litter devices of various widths can readily be used with the device of the present invention. As indicated in FIG. 2, when straps 52 and 54 are not in use, they are conveniently stowed within storage pockets P provided on the under surface of covering 14 (See the dotted lines in FIG. 2).

Also forming apart of the pediatric immobilization device of the present invention, is the provision of head support means for supporting the head of the infant or child. As best seen in FIG. 3, the head support means is here provided as a generally "U" shaped enclosure member 62 having a top panel 64 and two transversely spaced side panels 66 hingably connected to top panel 64. Each of the side panels 66 is provided with a lower marginal flap member which can be folded under the bottom side of cover 14 for interconnection with interconnection means provided on the lower surface of the cover. Turning to FIG. 4, this interconnection means can be seen to comprise a pair of longitudinally extending strips of fabric 68 each having a multiplicity of loops L. The lower flaps on each side panel 66 are in turn provided with strips of fabric having a multiplicity of hooks adapted to releasably engage loops L provided on members 68. A somewhat similar device is disclosed in U.S. Pat. No. 4,182,322 issued to the present inventor.

A forehead strap 70 is interconnected at one of its ends with one of the side panels 66 and is adapted to pass over the forehead of the infant in the manner shown in FIG. 3 for attachment to the opposite panel 66 by suitable interconnection means such as the previously described strips of fabric having a multiplicity of interengaging hooks and loops. Also forming apart of the head support means is a chin strap 72 one end of which is attached to a panel 66 in the manner shown in FIG. 3. Chin strap 72 passes beneath the chin of the infant and the free end of the strap is interconnected with the opposite panel 66 by suitable interconnection means such as cooperating hooks and loops.

In using the pediatric immobilization device of the invention with small children, of the character illustrated in FIG. 3, the infant is laid on the device with its head resting on portion 16 and its body resting on portion 28. Strap set 36 is strategically located so that when the device is used with very small children, the individual straps 36a and 36b can pass snugly over the chest of the infant.

It is important to note that straps 36a and 36b are of a narrow width so as to maintain a separation from the wider straps of strap set 40. With this arrangement a small child will be permitted to breathe freely even if the rescuer should apply straps 36a and 36b too snugly. Additionally, with a very small child of the character illustrated in FIG. 3, straps 40a and 40b can be conveniently passed over the legs and abdomen of the child to effectively immobilize the lower part of the child's body. Once strap sets 36 and 40 are in position, shoulder straps 44 can be passed about the shoulders of the infant and releasably interconnected to strap 36b. Finally, the head support means can be connected to the device in the manner previously described to immobilize the infant's head.

Turning now to FIG. 4, the device of the invention is there illustrated being used with a child of a slightly larger size than the child shown in FIG. 3. In using the device of the invention with this size child, straps 36a and 36b are still passed over the chest of the child. However, straps 40a and 40b are passed over the lower abdominal portion of the child, while straps 42a and 42b and 42c and 42d are used to immobilize each of the child's legs in the manner shown in FIG. 4. As clearly shown in the drawing, strap sets 36, 40 and 42 are strategically located so as to permit their use with children of an intermediate size. As indicated by the phantom lines in FIG. 4, when a somewhat larger child is to be immobilized on the device of the invention, strap set 42 is used to immobilize the upper portion of the child's legs while strap set 38 is used to immobilize the lower portions. Once again, shoulder straps 44 and the head support means of the invention are used in the manner previously described.

As illustrated in FIG. 7, when a still larger child is to be immobilized on the device, it becomes readily apparent that the pediatric sized device by itself is inadequate. At the same time, the adult sized device 50 is too large to provide correct immobilization of an accident victim of this size. It is in this instance that the pediatric device of the present invention is uniquely used in conjunction with the adult sized splint and litter device 50 to provide correct immobilization of the accident victim. When the devices are to be used together, the pediatric immobilization device of the present invention is interconnected with the adult sized litter device 50 in the manner previously described, and as illustrated in FIG. 5. It is important to note that the pediatric immobilization device of the present invention is of a length and width to enable it to be conveniently mounted on the adult sized litter 50 without in any way interfering with the operation of the adult litter. More particularly, the device of the present invention is of such width as to fit between the lifting apertures 60 provided on the adult litter and is of a length so as to not interfere in any way with the divided leg portions 50a and 50b of the adult litter, which enables the device to be used in connection with a standard Navy type litter basket. Stated another way, when the pediatric immobilization device of the present invention is used in conjunction with the adult sized litter 50, the combination can be used in exactly the same way, and for all of the purposes for which the adult sized litter device is used, as more fully described in U.S. Pat. No. 4,151,842.

In using the device of the present invention in combination with the adult sized litter device 50, the patient is secured to the interconnected devices in the manner illustrated in FIG. 7. More particularly, strap set 36 is used to pass over and secure the chest portion of the victim while strap set 40 is passed over the lower abdominal portion. As previously mentioned, the location of strap sets 36 and 40 is critical to proper immobilization of the patient without the danger of interfering with the patient's normal breathing. In using the combination device with a child of the size shown in FIG. 7, strap set 42 need not be used. However, strap set 38 is used to immobilize the upper leg portion of the victim in the manner shown. The lower leg portions of the patient can then be conveniently immobilized using straps 50c and 50d of the adult size litter 50. With this unique arrangement, the injury victim can be safely and securely immobilized using the combination of devices where neither device, by itself, would properly serve the purpose.

It is apparent from the study of FIGS. 3, 4, and 7 that by using various combinations of the strategically located restraining straps of the present invention, infants and children of various sizes can be safely immobilized on either the pediatric immobilization board by itself or on the interconnected pediatric device and the adult sized litter device. Accordingly, when the emergency vehicle such as an ambulance, fire truck, or the like, is provided with both the device of the present invention and the device of U.S. Pat. No. 4,151,842, accident victims of all ages and sizes can be accommodated.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A pediatric immobilization device for immobilization and transport of infants and small children, comprising:
    (a) a body support having spaced apart sides, a top, a bottom and head, neck, chest, abdomen and upper and lower leg portions;
    (b) carrying straps provided on said body support for use in lifting said device;
    (c) a first set of transversely spaced flexible restraining straps provided on said body support proximate said chest portion thereof said straps being constructed and arranged for emplacement substantially directly over the chest of an infant or of a small child positioned on said body support with the head resting on said head portion of said body support;
    (d) a second set of transversely spaced flexible restraining straps provided on said body support proximate said lower leg portion thereof;
    (e) a third set of transversely spaced flexible restraining straps provided on said body support intermediate said first and second set of straps and proximate said abdominal portion, said third set of straps having a width greater than the width of said first set of straps and being so constructed and arranged such that said third set of straps are of a width to span a substantial portion of the legs and abdomen of an infant having the head resting on said head portion of said body support said third set of straps being spaced from said first set of straps so as to not interfere with normal breathing;
    (f) a set of flexible shoulder straps provided on said support member proximate said first set of straps for restraining the shoulders of the infant or child;
    (g) a fourth set of flexible restraining straps provided on said body support and disposed intermediate said second and third sets of straps said fourth set of straps being so constructed and arranged and being of a width such that said straps can be emplaced over a substantial portion of, and substantially cover, the legs of a small child having the head resting on said head portion of said body support.

2. A pediatric immobilization device as defined in claim 1 in which said second set of flexible restraining straps provided on said body support are so constructed and arranged that said straps can be emplaced over the lower legs of a child of intermediate size having the head resting on said head portion of said body support.

3. An immobilization apparatus for immobilization and transport of infants, small children, large children, and adults, comprising:
 (a) a first immobilization unit comprising an adult body splint including:
  (i) a generally planar body support of a first width and length for supporting a large child and an adult, said body support having spaced apart sides, a top, a bottom and head, neck, chest, abdomen and upper and lower leg portions said leg portions being divided;
  (ii) lifting apertures provided on said body support for sue in lifting said immobilization apparatus;
  (iii) a set of transversely spaced flexible restraining straps provided on said body support proximate said lower leg portion thereof for emplacement over the legs of a large child having the head aligned with said head portion of said body support;
 (b) a second immobilization unit comprising a pediatric immobilization device removably connected in an overlaying relationship to said top of said first immobilization unit including:
  (i) a body support having a second width and length substantially less than that of said body support of said first immobilization unit for supporting an infant or small child said body support having spaced apart sides, a top, a bottom and head, neck, chest, abdomen and upper and lower leg portions;
  (ii) carrying straps provided on said body support for use in lifting said second immobilization unit;
  (ii) a first set of transversely spaced flexible restraining straps provided on said body support proximate said chest portion thereof for emplacement over the chest of an infant, small child, large child or adult having the head resting on said head portion of said body support;
  (iv) a second set of transversely spaced flexible restraining straps provided on said body support proximate said lower leg portion thereof for emplacement over the upper legs of a large child having the head resting on said head portion of said body support;
  (v) a third set of transversely spaced flexible restraining straps provided on said body support intermediate said first and second set of straps and proximate said abdominal portion, said third set of straps having a width greater than the width of said first set of straps and being located such that said third set of straps will substantially span the legs and abdomen of an infant having the head resting on said head portion of said body support;
  (vi) a fourth set of flexible restraining straps provided on said body support and disposed intermediate said second and third sets of straps said fourth set of straps being located and being of a width for emplacement over the legs of a small child having the head resting on said head portion of said body support; and
  (vii) a set of flexible shoulder straps provided on said support member proximate said first set of straps for restraining the shoulders of the infant, large child, or small child; and
 (c) connector means mounted on one of said first and second, immobilization units for removably interconnecting said first and second immobilization units in a position such that said head portion of said body support of said second immobilization unit overlays said head portion of said body support of said first immobilization unit.

4. An immobilization apparatus as defined in claim 3 in which said connector means comprises at least one pair of elongated strap means provided on said body support of said second immobilization unit for securing said second immobilization unit to said first immobilization unit.

5. An immobilization apparatus as defined in claim 4 in which said body support of said second immobilization unit comprises a rigid panel and cover means for covering said rigid panel, said cover means closely conforming to the shape of said rigid panel.

6. A pediatric immobilization device as defined in claim 5 in which said elongated strap means comprises an elongated first strap connected to one side of said cover means and a storage pocket provided on said cover means for storing said elongated strap when not in use.

7. A pediatric immobilization device as defined in claim 6 in which said elongated strap means further includes a second strap connected to said cover means on the opposite side thereof and having ring means for interconnectably receiving said first strap.

* * * * *